United States Patent
Carr et al.

(10) Patent No.: US 9,795,304 B2
(45) Date of Patent: Oct. 24, 2017

(54) LOW PROFILE TEMPERATURE TRANSDUCER

(71) Applicant: Meridian Medical Systems, LLC, Portland, ME (US)

(72) Inventors: Kenneth L. Carr, Woolwich, ME (US); Robert C. Allison, Rancho Palos Verdes, CA (US)

(73) Assignee: Coral Sand Beach LLC, Montclair, NJ (US)

( * ) Notice: Subject to any disclaimer, the term of this patent is extended or adjusted under 35 U.S.C. 154(b) by 417 days.

(21) Appl. No.: 14/364,513

(22) PCT Filed: Dec. 4, 2012

(86) PCT No.: PCT/US2012/067681
§ 371 (c)(1),
(2) Date: Jun. 11, 2014

(87) PCT Pub. No.: WO2013/090047
PCT Pub. Date: Jun. 20, 2013

(65) Prior Publication Data
US 2014/0343374 A1 Nov. 20, 2014

Related U.S. Application Data

(60) Provisional application No. 61/569,848, filed on Dec. 13, 2011.

(51) Int. Cl.
*G01K 1/16* (2006.01)
*G01J 5/00* (2006.01)
(Continued)

(52) U.S. Cl.
CPC ............ *A61B 5/01* (2013.01); *A61B 5/14552* (2013.01); *G01K 11/006* (2013.01);
(Continued)

(58) Field of Classification Search
CPC ................... G01J 5/12; G01J 5/20; G01J 5/44
(Continued)

(56) References Cited

U.S. PATENT DOCUMENTS 5,455,516 A * 10/1995 Jean ...................... G01N 22/04
324/636
6,111,520 A * 8/2000 Allen .................. B60C 23/0408
324/655
(Continued)

FOREIGN PATENT DOCUMENTS

WO   WO 86/04800 A1   8/1986

OTHER PUBLICATIONS

International Search Report and Written Opinion dated May 12, 201 for International Patent Application No. PCT/US2012/067681 filed on Dec. 4, 2012 by Meridian Medical Systems, LLC, 10 pages.

*Primary Examiner* — Gail Kaplan Verbitsky
(74) *Attorney, Agent, or Firm* — Wiggin and Dana LLP; Joseph Casino; Andrew D. Bochner (57) ABSTRACT

A low profile temperature transducer has a working surface for placement against a body surface and a first output. The transducer is a flat laminate composed of alternating conductive and dielectric layers. The laminate defines at least one slotline antenna for exposure to the body surface to pick up thermal emissions from the underlying tissue at depth. A feed network having a characteristic impedance is connected to the first output and a slotline-to-stripline transition is connected between the at least one antenna and the feed network, the transition providing a match between the impedance at the at least one antenna and the characteristic impedance. Also, a temperature sensor may be present at the working surface to detect the body surface temperature under the transducer, that surface temperature being used to calculate actual temperature at depth.

11 Claims, 8 Drawing Sheets

(51) Int. Cl.
*G01J 5/12* (2006.01)
*G01J 5/20* (2006.01)
*A61B 5/01* (2006.01)
*G01K 11/00* (2006.01)
*G01K 13/00* (2006.01)
*A61B 5/1455* (2006.01)
*A61B 5/00* (2006.01)
*H01Q 1/27* (2006.01)
*H01Q 13/10* (2006.01)
*A61F 7/00* (2006.01)
*A61F 7/02* (2006.01)

(52) U.S. Cl.
CPC .......... *G01K 13/002* (2013.01); *A61B 5/6814* (2013.01); *A61B 5/6831* (2013.01); *A61F 2007/0002* (2013.01); *A61F 2007/0056* (2013.01); *A61F 2007/0095* (2013.01); *A61F 2007/0288* (2013.01); *H01Q 1/273* (2013.01); *H01Q 13/10* (2013.01)

(58) Field of Classification Search
USPC ....... 374/121, 117, 122, 141, 183, 184, 185, 374/100, 170; 600/549, 474; 340/870.17
See application file for complete search history.

(56) References Cited

U.S. PATENT DOCUMENTS

| | | | |
|---|---|---|---|
| 6,463,336 B1* | 10/2002 | Mawhinney | A61N 1/40 600/14 |
| 7,637,656 B2* | 12/2009 | Billington | G01K 7/32 374/104 |
| 8,062,228 B2 | 11/2011 | Carr | |
| 8,834,020 B2* | 9/2014 | Abreu | A61B 5/0008 250/338.1 |
| 2008/0175300 A1* | 7/2008 | Billington | G01K 7/32 374/117 |
| 2012/0029381 A1* | 2/2012 | Carr | A61B 5/015 600/549 |
| 2013/0009848 A1* | 1/2013 | Plettemeier | H01L 23/66 343/893 |
| 2017/0065183 A1* | 3/2017 | Abreu | A61B 5/0008 |

* cited by examiner

LOW PROFILE TEMPERATURE TRANSDUCER

CROSS-REFERENCE TO RELATED APPLICATIONS

This application is the National Stage of International Application No. PCT/US2012/067681, filed on Dec. 4, 2012, which claims the benefit of U.S. Provisional Application No. 61/569,848, filed Dec. 13, 2011, the contents of both which are hereby incorporated herein by reference.

BACKGROUND OF THE INVENTION

Field of the Invention

This invention relates to apparatus for reliably detecting and monitoring the temperature of human or animal tissue, including but not limited to the brain of a neonatal patient.

Background Information

The development of early thermography or radiometry occurred at the IR frequency range, taking advantage of the higher levels of emission there. Nevertheless, detection at those frequencies and detection at millimeter and microwave frequencies are all considered to be passive microwave sensing for purposes of this application.

During pediatric cardiac surgery, it is usually necessary to obtain circulatory arrest so that no blood is flowing in the patient's blood vessels. In order to minimize the likelihood of injury to the patient's organs, particularly the brain, the patient is covered with a cooling blanket which reduces the patient's core temperature by hypothermic cooling prior to actual surgery. During surgery, the patient's heart is stopped and the intent is to maintain a brain temperature in the range of 15-18° C. Operating time is normally between 15 and 30 minutes. If the surgical procedure extends beyond that time, the infant's chances of survival decrease.

During the operation, since the patient's heart is stopped, there is no longer cold blood circulating through the blood vessels in the patient's brain. To prevent the patient's head being warmed by the ambient air of the operating room, during circulatory arrest, brain cooling is usually augmented by a cooling cap placed on the patient's head and through which a cooling fluid is circulated. All the while, a temperature sensor monitors the patient's brain temperature and the cooling may be adjusted in response thereto to maintain the desired temperature. Thus, the hypothermic cooling in combination with temperature monitoring can not only control brain temperature but also control the rate of cooling of the brain, as well as the rate to re-warm it.

There has recently been developed a dual mode intracranial temperature detection apparatus designed especially for neonatal patients. It uses microwave radiometry to monitor both intracranial temperature at depth and surface temperature enabling close control over the hypothermia process; see U.S. Pat. No. 8,062,228, the entire contents of which are hereby incorporated herein by reference.

A patient's core temperature is usually measured by a rectal or esophageal temperature probe. However, quite often due to trauma or insult, the brain temperature is elevated so that a temperature measurement at those remote locations is no longer a reliable indication of brain temperature. What is needed is a better way to measure brain temperature at depth. In a study, we found that to do so, it became necessary to establish a relationship between core temperature, surface temperature and radiometric temperature thereby allowing a determination of temperature verses depth in the target tissue, e.g. the brain.

Figure 7:
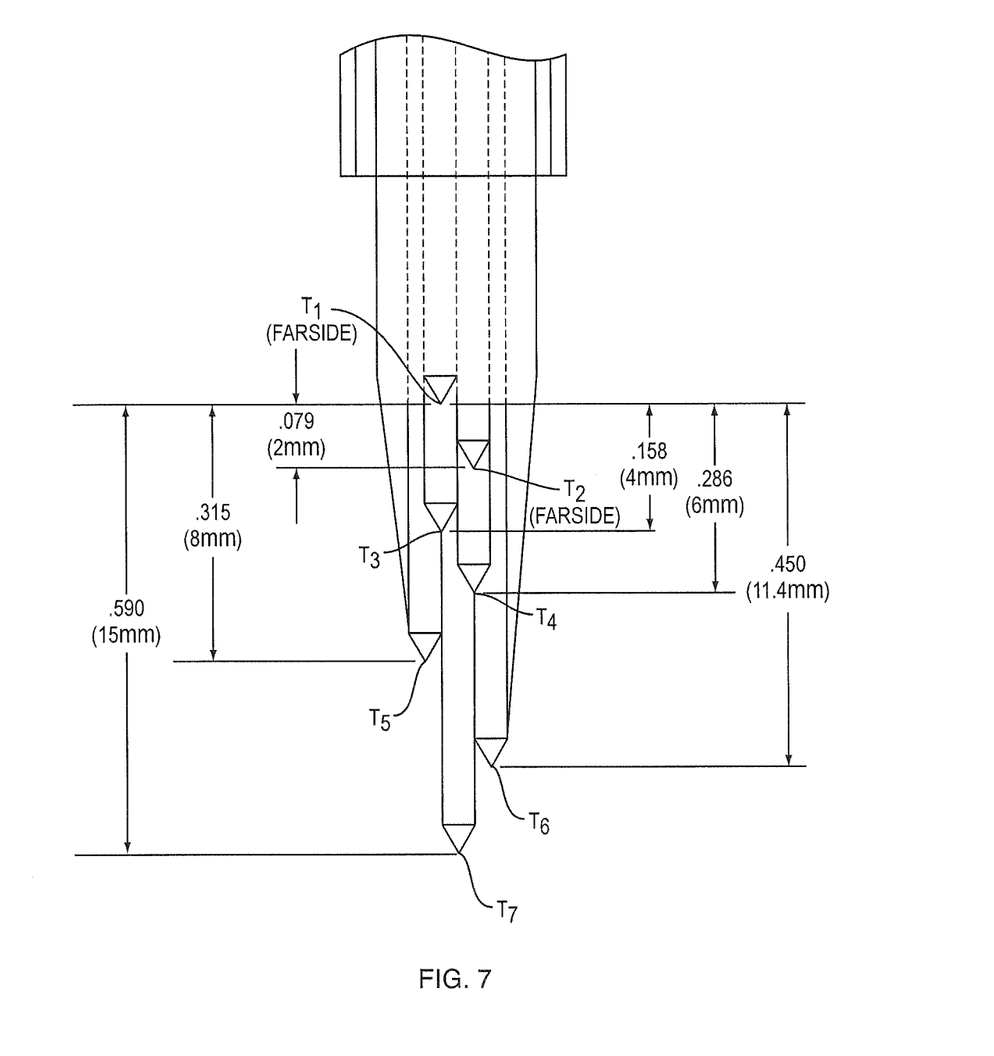
FIG. 7, already described, is a diagrammatic view of a thermocouple probe used in animal studies to develop a temperature-at-depth algorithm for processing the output of the FIG. 1 transducer.

FIG. 7 is a diagrammatic view of the temperature probe used in that study. It includes seven thermocouples $T_1$ to $T_7$ which were inserted to the indicated depths in the head of a young anesthetized pig. The temperature versus depth curves shown in FIG. 8 were derived from the thermocouple measurements. We found that the difference in temperature between the 2 mm (near surface) and the temperature deep within the brain was about 2° C. and that the curve for both the normothermic otherwise and cooled animal was identical.

Figure 8:
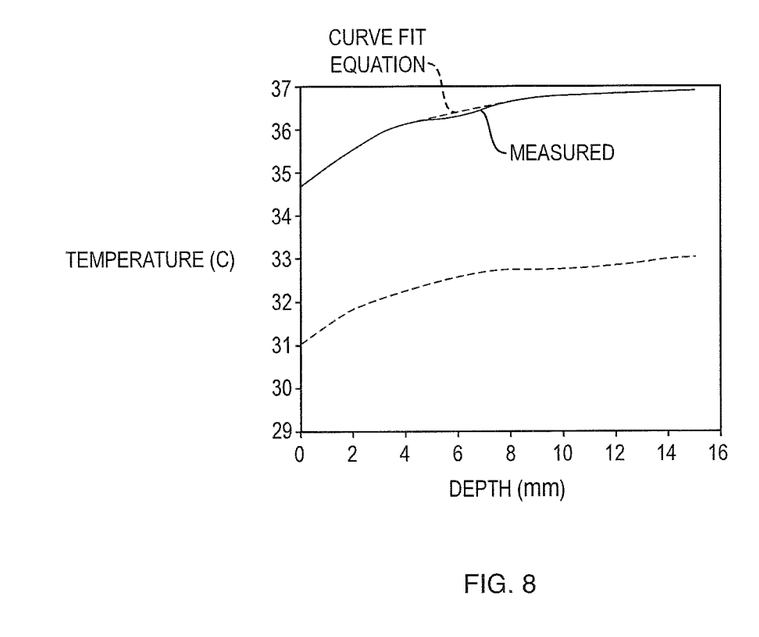
FIG. 8, already described, in a graph of temperature versus depth used with the FIG. 7 probe, and FIG. 9 already described, is a graph showing the antenna factor used to develop the temperature-at-depth algorithm.
Figure 9:
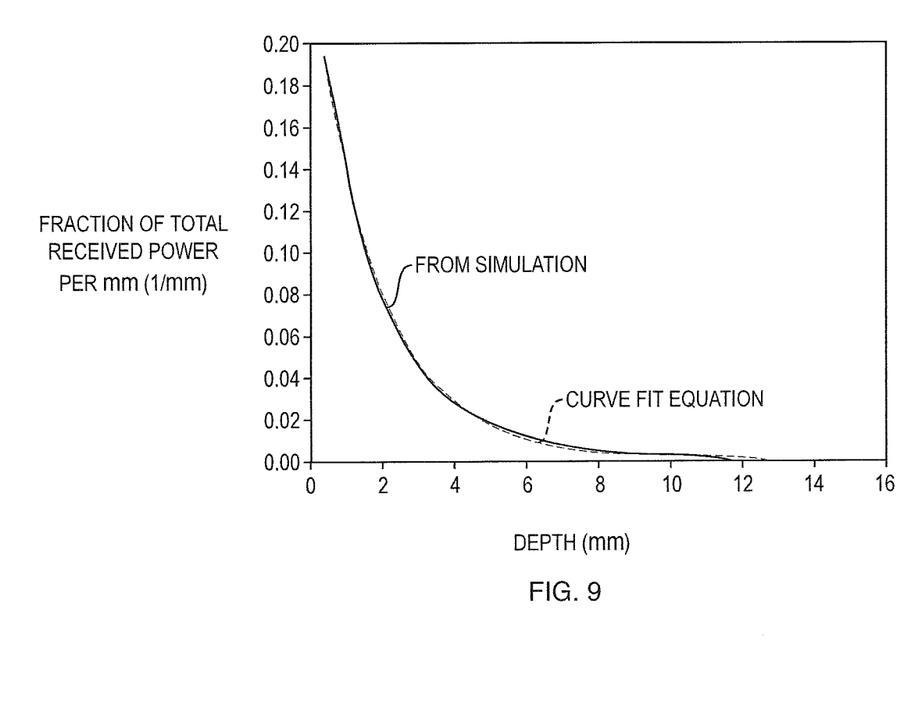

FIG. 9 shows the fraction of total received signal power versus target tissue depth from antenna simulations. The radiometer does not measure the temperature at a specific point. Rather, it measures the average temperature based on the antenna pattern. This average temperature is the summation for all depths of the received power contributions from FIG. 9 multiplied by the temperatures at each depth from FIG. 8. With that and the surface temperature, the temperature at depth may be calculated from:

Deep Depth

T radiometer=$\int_{0depth}^{40\ mm}$ antenna factor×temp. at depth×d(depth)

where:

antenna factor=fraction of total received power per mm of depth from FIG. 9;

temperature at depth =temperatures from FIG. 8.

The above-described patented apparatus employs a microwave transducer designed to be positioned on the patient's head. However, if the patient is wearing a cooling blanket and/or cap as described the transducer, which has a relatively high profile, e.g. 2.5 cm, protrudes appreciably from the patient's head. This protrusion makes attachment of the device to the patient somewhat difficult and also interferes with the cooling blanket and/or cap in that it lifts the cooling blanket/cap away from the patient's head which results in improper cooling of the patient in the region where the transducer is applied.

Accordingly, there is a need to provide apparatus which can monitor a patient's intracranial and near surface temperatures using a single, low profile transducer able to be affixed to the patient's forehead without interfering with any EEG electrodes present on the patient's scalp and without lifting a cooling cap or blanket covering the patient's cranium.

SUMMARY OF THE INVENTION

It is thus an object of this invention to provide an improved cerebral temperature transducer for monitoring a patient's brain tissue temperature.

Another object of the invention is to provide such a transducer which has an especially low profile so that it does not protrude appreciably from the forehead of a small patient such as a neonate.

A further object of the invention is to provide a cerebral temperature transducer which does not interfere with ancillary medical devices such as EEG electrodes, cooling/warming coverings and the like.

Still another object of the invention is to provide a transducer of this type which can sense both deep and near surface temperatures of a selected area of a patient's body.

Other objects will, in part, be obvious and will, in part, appear hereinafter.

The invention accordingly comprises the features of construction, combination of elements and arrangement of parts which will be exemplified in the construction hereinafter set forth.

Briefly, the present apparatus includes a temperature transducer which has an especially low profile enabling it to be releasably affixed to the forehead of a patient. While the apparatus has particular application to measuring the cerebral temperature of small patients such as neonates, it may also be used on adults and at other locations on the body.

The transducer includes one or more slotline antennas arranged and adapted to pick up thermal emissions from relatively deep in the patient's tissue as well as a separate sensor arranged to detect the skin or near surface temperature of the patient. The transducer is shaped and dimensioned so that it does not appreciably lift a cooling blanket or clothing that may cover the patient or otherwise interfere with ancillary sensors and other medical devices affixed to the patient.

In use, the transducer is connected to an external control unit which produces output signals reflecting the skin temperature and temperature at depth of the target area over to control a display which can present the two temperature to surgical personnel.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
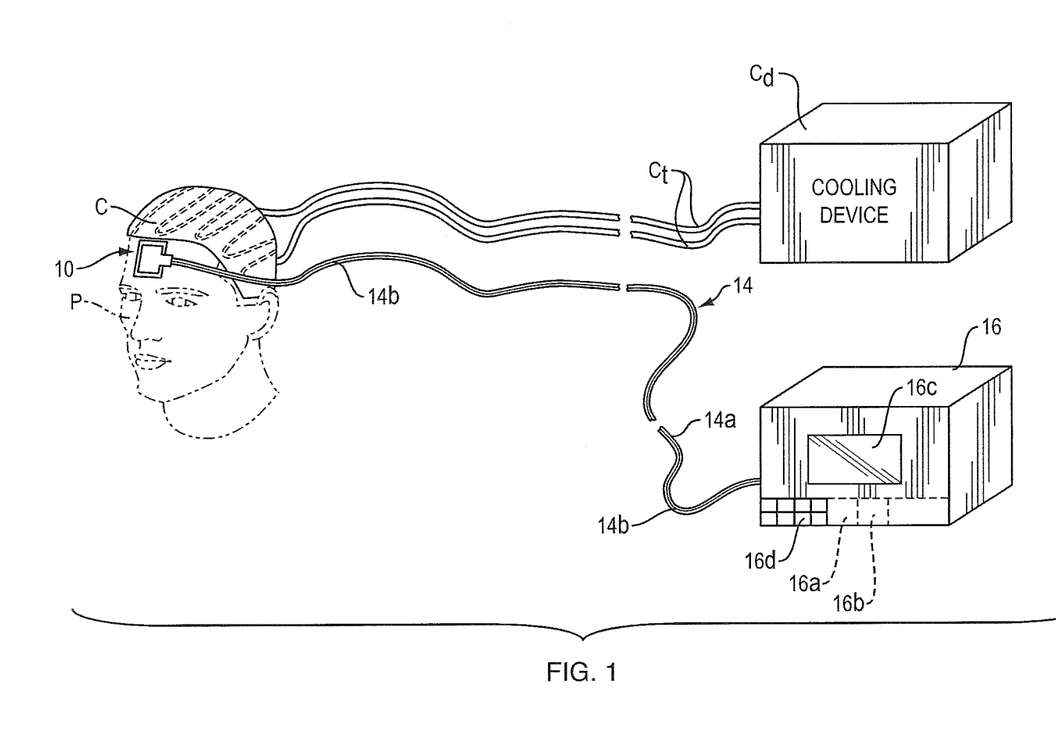
FIG. 1 is a diagrammatical view of monitoring apparatus comprising a dual mode temperature transducer incorporating the invention.
Figure 2:
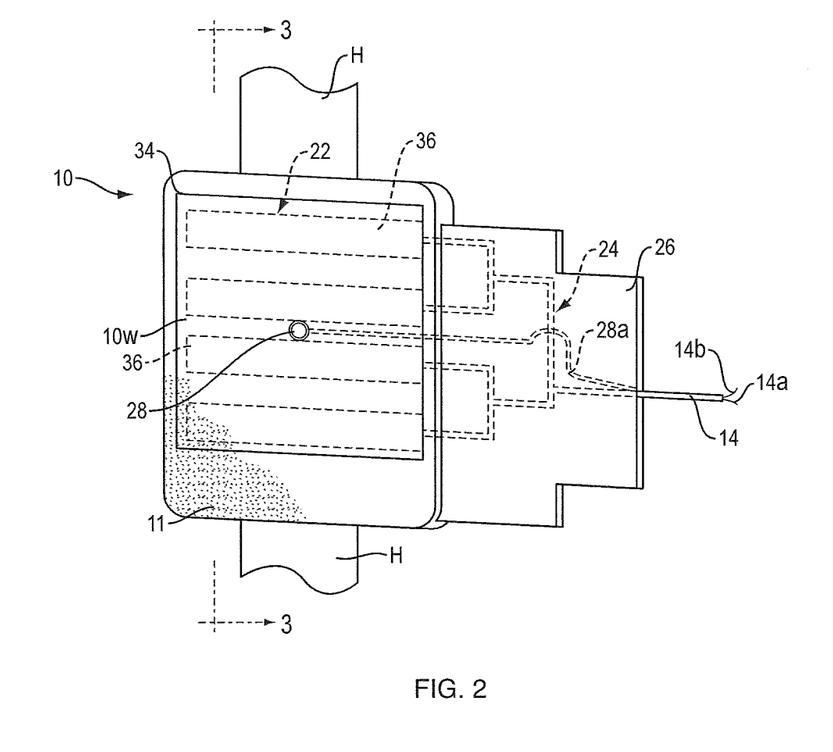
FIG. 2 is a perspective view from below, on a larger scale, showing the transducer in greater detail.

Referring to FIGS. 1 and 2 of the drawings, the present apparatus includes a flat, low-profile, plural-layer laminated transducer shown generally at 10 which may be removably affixed to the forehead of a patient P, such as a neonate in preparation for pediatric cardiac surgery. Of course, the transducer may also be affixed to other parts of a human or animal body to measure the temperatures of the underlying tissue.

As best seen in FIG. 2, the transducer 10 may have a working surface $10_w$ formed to fit the contour of the placement site, in this case the forehead of patient P. The transducer may be held in place by an adhesive indicated by stippling 11 on surface $10_w$ and/or by an adjustable, and possibly flexible, headband H attached to the transducer and releasably engaged around the patient's head. If desired, the transducer including the headband may be formed as a low cost, disposable, one-time-use unit.

Also, it is sometimes desirable that a shallow dome (not shown) be present at the working surface $10_w$ of transducer 10 to minimize the likelihood that an air pocket will form between the transducer 10 and the skin surface of patient P.

Should the surface tissue of patient P not be sufficiently soft to allow proper placement of the transducer, a disposable interface similar to the interface described in the above patent may be interposed between the transducer and the patient.

As shown in FIG. 1, during surgery, the patient's cranium is preferably covered by a cooling cap or blanket C connected via tubing $C_t$ to a cooling device $C_d$ which circulates a cooling fluid through the cap or blanket to cool the patient's brain to maintain a low temperature in the order of 15-18° C.

As we shall see, transducer 10 contains a pair of temperature sensors capable of detecting temperatures at two different depths in the patient's cranium, i.e. a temperature at depth (at least 15 mm deep) and a near surface or skin temperature (about 2 mm deep), and producing corresponding output signals which are coupled via a cable 14 to a control unit 16. That unit includes a radiometric receiver 16a which, under the control of a processor/controller 16b, produces an output signal which reflects the brain temperature at depth. The processor/controller also receives the output of the near surface sensor and produces a signal reflecting the near surface temperature. Unit 16 may also include a display 16c which responds to those signals to provide a visible indication of the two temperatures. Unit 16 may be turned on and off and controlled by way of a keypad 16d.

The temperature detecting component of transducer 10 which detects temperature at depth comprises a stripline antenna assembly shown generally at 22 in FIGS. 2 and 4 and which will be described in detail later. This assembly receives microwave emissions picked up by the assembly from relatively deep in the patient's cranium. These signals are combined in a feed network 24 on a circuit board 26 extending from the transducer 10 before being applied to a conductor 14a of cable 14. Preferably, that feed network appendage 24, 26 does not contact the patient's body.

On the other hand, the sensor for detecting the near surface temperature may comprise a conventional thermistor, thermocouple or infrared (IR) sensing device 28 placed at or near the center of the transducer's working surface $10_w$ so that it will not perturb the aperture of antenna assembly 22. One suitable tiny (1.6 mm²) IR chip is Model TMP006 made by Texas Instruments. The device 28 may be connected by printed paths 28a on circuit board 26 to conductor 14b of cable 14.

When the transducer 10 is in contact with the patient's cranium as shown in FIG. 1, the device 28 senses the temperature at a single location near the surface of the patient's cranium. Also, the antenna assembly 22 creates a desirably shaped microwave field pattern extending relatively deep in the patient's brain tissue. This allows the collection of microwave energy for determining the temperature within the volume of the field pattern relatively deep in the patient's cranium using microwave radiometry.

Thus, transducer 10 is an advance over the previous transducer designs in that the physical volume and weight of the transducer are much less than those of prior dielectric-loaded waveguide transducers such as the ones disclosed in the above patent. More particularly, the thickness of the transducer 10 above the patient's skin is quite small, typically less than 2 mm, and the contact area between the transducer and the skin is also minimized, i.e. 3.14 cm² vice 5.53 cm². As we shall see, transducer 10 functions also to provide an impedance transformation or match from the body tissue impedance to a convenient microwave transmission line impedance, e.g., 50 ohms.

Figure 3:
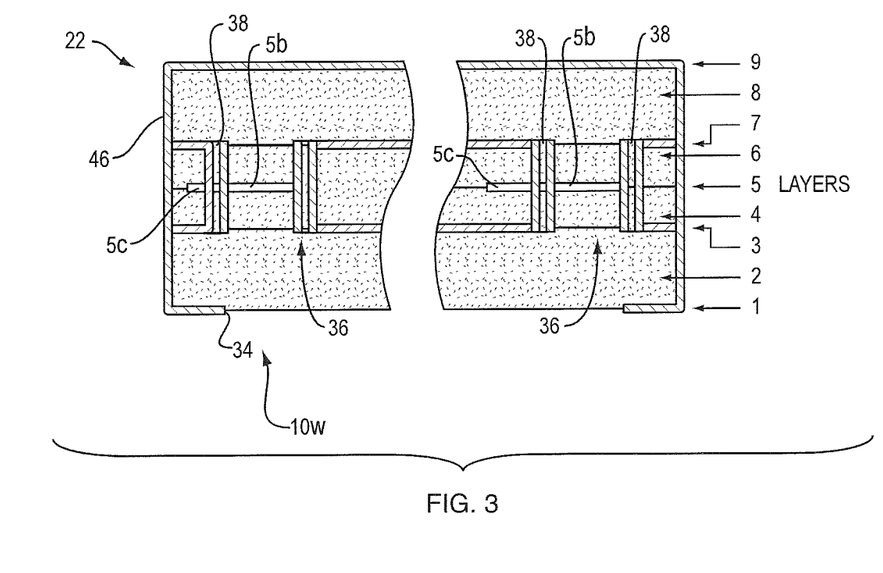
FIG. 3 is a sectional view taken along line 3-3 of FIG. 2, on a still larger scale, depicting the individual layers 1 to 9 of the transducer.
Figure 4:
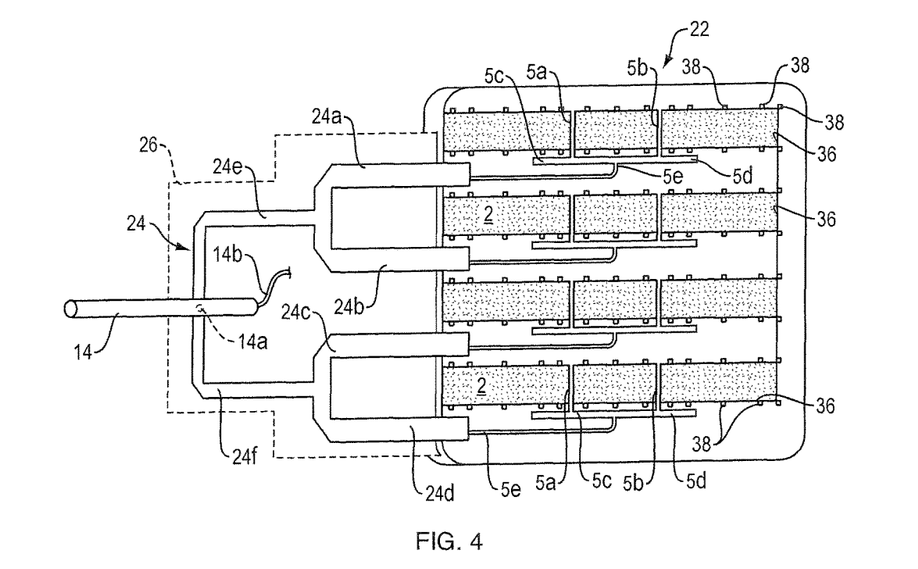
FIG. 4 is a bottom plan view of the transducer in FIG. 3 with layers 6-9 thereof removed.

Refer now to FIGS. 3 and 4 which show transducer 10 in greater detail. It comprises alternating layers of dielectric material and metal plating that can be manufactured using conventional multilayer circuit board technology. In FIG. 3, the metal layers are layers 1, 3, 5, 7 and 9 and the dielectric layers are layers 2, 4, 6 and 8. In FIG. 4 (and FIG. 5), the stippled areas comprise layer 2. The illustrated dielectric layers are of a low loss material. The circuit board extension 26 mentioned above may be an extension of the dielectric layer 4 or 6. The dielectric layers 2 and 8 may have a thickness in the order of 20 mils, while the dielectric layers 4 and 6 may be as thin as 5 mils. The metal layers may have a thickness of about 1 mil.

The metal layer 1 at the working surface $10_w$ of the transducer faces the patient's skin and defines an aperture 34 of the transducer 10 that allows the microwave fields emanating from the patient to pass through to an array of metal slots 36 in metal layers 3 and 7 that comprise slotline antennas. These layers 3 and 7 constitute ground conductor layers forming a stripline structure comprised of layers 3, 4, 5, 6 and 7, the structure converting the microwave fields to stripline transmission line signals. In the illustrated transducer, there are four slots 36. However, there could be more or less depending upon size of the aperture 34 and the particular application. The primary mode in each slot transmission line or antenna formed by a slot 36 is the TE mode. As noted above, the skin temperature sensor 28 is located in the center area between adjacent slots 36 so that it does not perturb the transmit/receive paths of those antennas.

Figure 5:
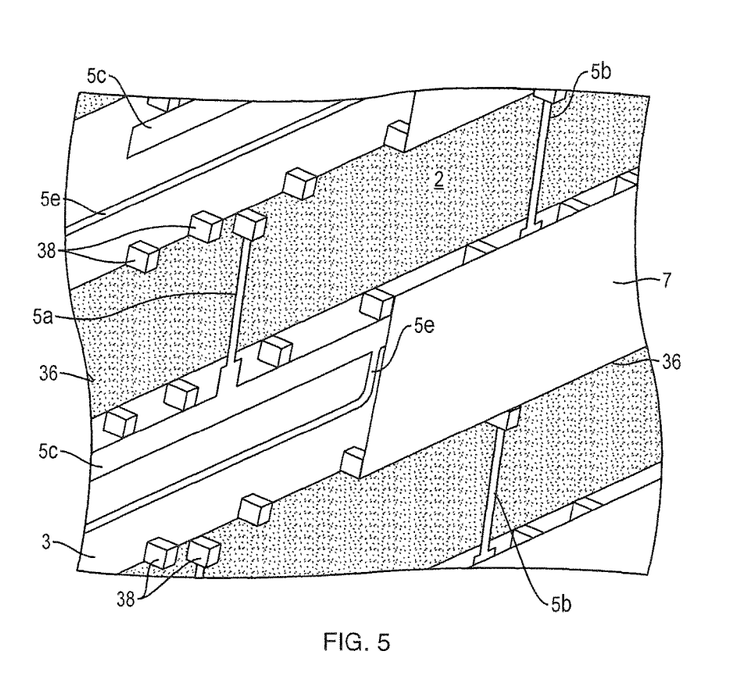
FIG. 5 is a fragmentary perspective view, on an even larger scale, of the FIG. 3 transducer with layers 8 and 9 and half of layers 6 and 7 removed to show layer 5.

As shown in FIGS. 3 to 5, the two metal layers 3 and 7 are electrically connected together by metal plated holes 38 in the dielectric layers 4 and 6, the holes being spaced apart around the peripheries of the slots 36. In FIG. 5, layers 4, 6 and half of layer 7 have been removed for clarity and the holes 38 are shown as having square cross sections, but the cross-section could also be round or some other shape.

Metal layer 5, which is midway between ground layers 3 and 7, is the stripline conductor layer. It may be printed on either layer 4 or 6. Layer 5 forms two stripline conductors 5a and 5b which span each slot and connect to the ground layers 3 and 7 on one side of the associated slot by way of selected ones of the plated holes 38 to form the transition from slot transmission line to stripline with impedance matching. These two conductors are optimally located along the corresponding slot to produce a desirable body tissue field pattern in the direction of the slot length.

As best seen in FIGS. 4 and 5, the stripline conductors 5a and 5b at each slot connect to impedance matching circuits created from stripline stubs 5c and 5d formed by metal layer 5 to efficiently couple the slot transitions to the characteristic impedance of the stripline feed network 24. More particularly, the two stubs at the uppermost slot 36 are connected by a bridging trace 5e to one leg 24a of feed network 24. Similar traces 5e associated with the other three slots 36 are likewise connected to branches 24b-24d, respectively, of network 24. The branches 24a and 24b are combined at a leg 24e of the network and the branches 24c and 24d are combined at a leg 24f and the outputs of those legs are combined at conductor 14a of cable 14 which carries the two transducer outputs.

Thus, the network 24 is a reactive power combiner network that brings the signals from each of the stripline/slot transitions in transducer 10 together at a single output. If additional bandwidth is required, this network may be replaced by a broad band Wilkinson combiner network; See H. Howe, "Stripline Circuit Design," pp. 94, 95. In the illustrated transducer 10, the output transitions to a coaxial cable, but it could transition to a connector or other conventional transmission line scheme. In any event, the feed network 24 and the stubs and traces 5c to 5e and 28a formed by the metal layer 5 are routed in the stripline areas between the slots 36 to avoid interfering with the slot function.

The dielectric layer 8 best seen in FIG. 3 forms a dielectric-filled cavity with the metal layer 9 behind the stripline. Edge plating 46 connects metal layers 1 and 9 to form a grounded metal enclosure or shield around the transducer 10 to exclude interference from exterior sources. Spaced-apart plated through holes or screws (not shown) in the dielectric layers connecting layers 1 and 9 at the peripheries thereof could also perform this function.

Although the illustrated transducer has four slots 36, each fed by a pair of stripline conductors 5a, 5b, other numbers of slots and feed points (conductors 5a, 5b) are possible depending upon the particular application. As mentioned above, the transducer 10 should conform to the shape of the patient's cranium. To facilitate this, the dielectric layers 2, 4, 6 and 8 may be of a somewhat pliable or conformable material such as Rogers 5880 material.

Figure 6A:
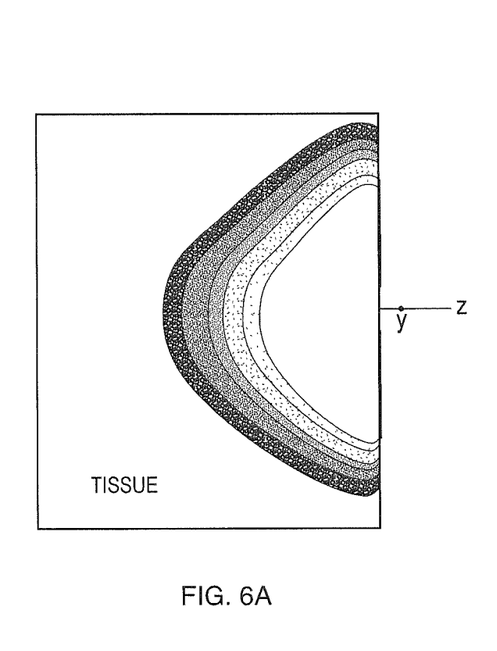
FIGS. 6A and 6B together illustrate an antenna field pattern that may be produced by the transducer.
Figure 6B:
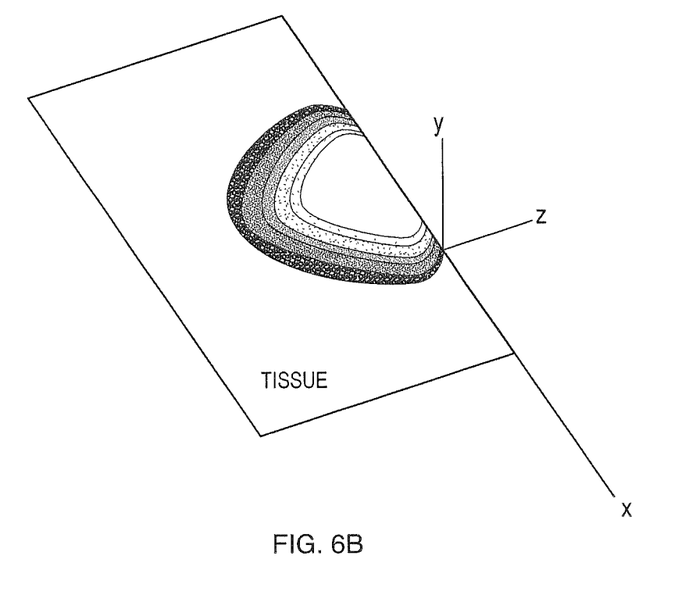

Each slot 36 produces a dipole-like antenna pattern and the patterns of the four slots are additive. FIGS. 6A and 6B illustrate the shape of combined field pattern produced by the four-slot antenna assembly 22, taken along the Y/Z and X/Z axes, respectively.

In control unit 16 (FIG. 1), the output of the antenna assembly 22 is applied to radiometer 16a under the control of the processor/controller 16b to cause the display 16c to display the temperature at depth in the patient's cranium. At the same time, the output signal from sensing device 28, representing the near surface temperature of the patient, is coupled to display 16c so that both intracranial temperature and the near surface temperature of patient P are presented simultaneously to medical personnel. Desirably, the processor/controller 16b, using the algorithm described above, processes the near surface temperature signal from sensing device 28 and the intracranial temperature provided by the radiometer to provide a more accurate representation of the temperature at depth that is displayed by display 16c.

It will thus be seen that the objects set forth above among those made apparent from the preceding description are efficiently attained. Also, certain changes may be made in the above construction without departing from the scope of the invention. For example, slot(s) 36 may be present only in metal layer 3 in which case layers 6 and 7 may be omitted thereby placing layer 8 against layer 5. Also, the transducer may incorporate an oxygen saturation sensor as described in application No. 13/459,391, filed Apr. 30, 2012, the contents of which is hereby incorporated herein by reference. Therefore, it is intended that all matter contained in the above description or shown in the accompanying drawings shall be interpreted as illustrative and not in a limiting sense.

The invention claimed is:

1. A low profile temperature transducer having a working surface for placement against a body surface to pick up thermal emissions at a depth below the body surface and produce a corresponding transducer output, said transducer comprising a flat laminate composed of alternating conductive and dielectric layers which define at least one slotline antenna adapted to receive thermal radiation emanating from a depth below the body surface and produce a corresponding antenna output, a feed network having a characteristic impedance connected to said transducer output and a slotline-to-stripline transition connected between the at least one antenna and the feed network, said transition providing a match between impedance at the at least one antenna and said characteristic impedance, wherein the flat laminate includes:
a first metal layer at the working surface that defines an antenna aperture:
a second metal layer beyond the first metal layer is slotted to form the at least one antenna, the first metal layer and the second metal layer being grounded:
a third metal layer beyond the second metal layer that includes said feed network and said
transition: and
a fourth metal layer beyond the third metal layer is slotted in the same configuration as the second metal layer and the corresponding slots of the second metal layer and the fourth metal
layer are connected electrically at slot perimeters thereof to form the at least one antenna.

2. The transducer defined in claim 1 wherein
said transition comprises a pair of stripline traces which bridge each slot antenna at selected spaced-apart locations along the length thereof, one of each stripline trace being connected to the second metal layer, and a stub trace connected to the other end of each stripline trace to provide said impedance match, and
said feed network comprises electrical connections between the stub traces associated with each pair of stripline traces and said transducer output.

3. The transducer defined in claim 2 wherein
said at least one antenna comprises two or more similar antennas, and
the feed network combines the outputs of all of the two or more similar antennas at said transducer output.

4. The transducer defined in claim 1 wherein plated through holes are provided in the dielectric layers between the second metal layer and the fourth metal layer to electrically connect the slot perimeters of the second metal layer and the fourth metal layer.

5. The transducer defined in claim 1 wherein said first metal layer is part of a grounded conductive shield that surrounds all the other layers to exclude outside electrical effects.

6. The transducer defined in claim 1 and further including a temperature sensor affixed to said working surface for sensing the temperature of the body surface under the transducer, an output of the sensor constituting a second transducer output.

7. The transducer defined in claim 6 wherein said sensor is selected from the group consisting of an infrared sensor, a thermistor and a thermocouple.

8. The transducer defined in claim 1 and further including a blood oxygen saturation sensor at said working surface.

9. A temperature measuring apparatus comprising
the transducer defined in claim 1, and a radiometer connected to receive the transducer output and produce a corresponding temperature signal and a processor for processing the temperature signal and said sensor output to provide an indication of the actual temperature at depth under the transducer.

10. A low profile temperature transducer for determining intracranial temperature by picking up thermal emissions at a depth below a cranium surface and producing a corresponding transducer output, said transducer formed to fit a contour of the cranium surface and comprising a flat laminate composed of alternating conductive and dielectric layers which define at least one slotline antenna adapted to receive thermal radiation emanating from below the cranium surface and produce a corresponding antenna output, a feed network having a characteristic impedance connected to said transducer output and a slotline-to-stripline transition connected between the at least one antenna and the feed network, said transition providing a match between impedance at the at least one antenna and said characteristic impedance, wherein the flat laminate includes an antenna aperture arranged to allow microwave fields emanating from the depth below the cranium surface to pass through to the slotline antenna, and wherein a first metal layer defines the antenna aperture, a second metal layer beyond the first metal layer is slotted to form the at least one antenna, said first and second layers being grounded, and a third metal layer beyond the second metal layer includes said feed network and said transition, said transition comprising a pair of stripline traces which bridge each slot antenna at selected spaced-apart locations along the length thereof, one of each stripline trace being connected to the second metal layer, and a stub trace connected to the other end of each stripline trace to provide said impedance match, and said feed network comprising electrical connections between the stub traces associated with each pair of stripline traces and said transducer output.

11. The transducer defined in claim 10 wherein:
said at least one antenna comprises two or more similar antennas, and
the feed network combines the outputs of all of the two or more similar antennas at said transducer output.

* * * * *